(12) United States Patent
Larsson et al.

(10) Patent No.: US 7,244,387 B2
(45) Date of Patent: Jul. 17, 2007

(54) APPARATUS AND METHOD FOR MANUFACTURING AN ABSORBENT CORE

(75) Inventors: Gunnar Larsson, Landvetter (SE); Goran Forsbring, Kungsbacka (SE)

(73) Assignee: SCA Hygiene Products AB, Gothenburg (SE)

( * ) Notice: Subject to any disclaimer, the term of this patent is extended or adjusted under 35 U.S.C. 154(b) by 393 days.

(21) Appl. No.: 10/905,756

(22) Filed: Jan. 19, 2005

(65) Prior Publication Data

US 2005/0167874 A1 Aug. 4, 2005

Related U.S. Application Data

(60) Provisional application No. 60/540,655, filed on Feb. 2, 2004.

(51) Int. Cl.
*A61F 13/15* (2006.01)

(52) U.S. Cl. ............... 264/517; 264/518; 264/113; 264/121; 425/80.1; 425/81.1; 425/83.1

(58) Field of Classification Search ............... None
See application file for complete search history.

(56) References Cited

U.S. PATENT DOCUMENTS

| | | | | |
|---|---|---|---|---|
| 4,908,175 | A * | 3/1990 | Angstadt | 264/113 |
| 5,236,430 | A | 8/1993 | Bridges | |
| 5,447,677 | A | 9/1995 | Griffoul et al. | 264/510 |
| 5,779,831 | A | 7/1998 | Schmitz | |
| 6,652,798 | B1 | 11/2003 | Edvardsson | |
| 2002/0168909 | A1 * | 11/2002 | Edwardson et al. | 442/208 |
| 2003/0022582 | A1 | 1/2003 | Cree et al. | |
| 2004/0061264 | A1 * | 4/2004 | Heyn et al. | 264/518 |
| 2004/0102757 | A1 | 5/2004 | Olson | |
| 2006/0271009 | A1 | 11/2006 | Cartier et al. | |

FOREIGN PATENT DOCUMENTS

| | | |
|---|---|---|
| EP | 0 297 180 A1 | 1/1989 |
| EP | 0 627 211 A1 | 12/1994 |
| WO | WO 03/047488 A1 | 6/2003 |
| WO | WO 03/053297 A2 | 7/2003 |
| WO | WO 2005/122984 A1 | 12/2005 |
| WO | WO 2005/122985 | 12/2005 |
| WO | WO 2006/093444 | 9/2006 |

OTHER PUBLICATIONS

An International Search Report issued in a corresponding application.
U.S. Appl. No. 11/630,371; Hildeberg et al.; filed Dec. 21, 2006.
U.S. Appl. No. 11/630,372; Wastlund-Karlsson et al.; filed Dec. 21, 2006.
International-Type Search Report dated Sep. 15, 2004.

* cited by examiner

*Primary Examiner*—Mary Lynn Theisen
(74) *Attorney, Agent, or Firm*—Buchanan Ingersoll & Rooney PCV

(57) ABSTRACT

An apparatus and a method for manufacturing an absorbent core for an absorbent product containing a first material and a second material dispersed throughout at least a portion of said first material. A rotating forming wheel produces the absorbent core in a mold provided on its circumferential surface and the forming wheel has a rotating air pervious belt along at least a part of the circumferential surface for keeping fibers and particles of the formed layer or layers in place on the wheel.

19 Claims, 2 Drawing Sheets

APPARATUS AND METHOD FOR MANUFACTURING AN ABSORBENT CORE

CROSS-REFERENCE TO RELATED APPLICATIONS

The present application claims the benefit of U.S. Provisional Application No. 60/540,655, filed in the United States on Feb. 2, 2004, the entire contents of which are hereby incorporated herein by reference.

TECHNICAL FIELD

The present invention relates to a method and an apparatus for the manufacturing of an absorbent core containing particles of a second material, such as super absorbent polymers (SAP), dispersed within a first absorbent material. More specifically, the present invention is directed to the manufacture of an absorbent core with the object of reduction of losses of the second material during manufacture.

BACKGROUND OF THE INVENTION

Absorbent products, such as diapers, training pants, napkins, incontinence pads and the like, contain an absorbent core usually comprising a soft, fluffy material, such as comminuted wood pulp fibers. Various secondary materials are often incorporated into the absorbent fluff material, such as particles of superabsorbent polymers (SAP), heat activatable bonding fibers or odour absorbent material. Super absorbent materials are polymers having the ability to absorb water and bodily fluids many times there own weight. The super absorbent material is either mixed with the fluff pulp fibers or applied in a layered configuration between layers of fluff pulp.

One way to produce such an absorbent core containing a second material is to form a first layer of absorbent fluff pulp, whereupon the second material is sprinkled on top of the fluff pulp. A second layer of absorbent fluff pulp is then placed on top of the second material to complete the core. The absorbent core may further comprise two or more layers of the second material disposed between layers of absorbent fluff pulp fibers. A result of this method is that it produces a product with a layered configuration, in which the second material is concentrated in fairly discrete zones within the core.

Alternatively, the second material (such as SAP particles) is mixed with and distributed throughout the first material (the absorbent fluff pulp fibers). It is further known to make absorbent products including a first and a second layer, in which the first layer contains a pure first material and the second layer contains a mixture of the first and the second material.

One way to produce an absorbent core for products with a fairly uniform distribution of the second material within the core is disclosed in patent document U.S. Pat. No. 5,447,677. All statements and drawings in said document are hereby included, by reference, in this description. In said disclosure there is presented an apparatus for making absorbent products containing a first material, such as absorbent fluff from wood pulp fibers. Said absorbent fluff pulp is introduced into a vacuum-forming chamber. A portion of the fluff pulp is deposited into the cavity of a mold transported through the forming chamber by a forming wheel so as to form a layer of pure fluff pulp within the bottom of the mold cavity. A second material, such as superabsorbent particles or heat activatable bonding fibers, is introduced into the forming chamber so that streams of the first and second materials collide within a mixing zone. As the mold continues it travels through the forming chamber. A mixture of first and second materials from the mixing zone is deposited within the mold cavity, thereby filling it. The result is an absorbent core having a first layer formed by pure first material and a second layer formed by a mixture of the first and second materials.

A more detailed description of a known manufacture of an absorbent product of the design as discussed is made here by reference to FIG. 1. From a defibration unit pulp fibers are transported by the aid of air up to hoods 1a, 1b and through the hoods towards a forming wheel 3. The forming wheel 3 is provided with stationary suction boxes 2, wherein very low pressure prevails. The suction boxes face said hoods containing the pulp fibers. On the surface of the forming wheel 3 an air pervious means, such as a net or a perforated plate, is provided. When said air pervious means rotates, in the direction shown by the arrow 3b, under said hoods the pulp fibers are forced by an air stream towards the air pervious means and form a core of pulp fibers along the circumference of the forming wheel in the shape of a continuous mat. Said circumference may be provided with molds for forming separate absorbent cores of different designs.

The core may further be formed into several layers by the use of several hoods. The core may, as stated, be formed into discrete cores or if a continuous mat-formed core is formed, it may be later cut into the desired design.

A flow of SAP-fibers is added to the pulp fibers by an injection of the SAP-fibers through a pipe 4 into one or more of the hoods 1. After the last hood (in the figure hood 1b) the core formation is completed and the core is kept in the mold or molds on the wheel by means of an underpressure in a second stationary suction box 5. The core is, after the passage past said second suction box 5, transferred to a transfer drum 5a, where it may be compressed, for example by means of a mechanical pressure exerted on the core during its passage over the transfer drum. Finally, the core is transferred to a conveyor 6 for further treatment or packaging. Transfer from the forming wheel 3 to the conveyor 6 may be to undertaken without the transfer drum.

An end product may consist of several cores, whereby the manufacturing assembly for said end product consists of two or more forming wheels 3, each one of the wheels forming a core, whereupon the two or more resulting cores are assembled to the end product.

A disadvantage in the discussed manufacturing process is that SAP-particles or fibers are easily lost from the core after the completion of the core formation on the forming wheel 3 along the distance the core travels until it is transferred to the conveyor. Even if a very high vacuum is utilized in the second suction box 5, it is very difficult to retain all of the SAP-particles in the formed core, especially if high speeds are used for the transporters, that is, the conveyor, the forming wheel and the transfer drum. Arrangements may be made to collect the lost SAP-particles in funnels. In this way, portions of the lost amount of SAP-particles are collected and may be returned to the core forming process. Other portions of the lost SAP-particles must be discarded. Still other portions of said particles land on the machinery, whereby the machinery has to be cleaned regularly. SAP-particles may also fall down on an underlying conveyor, which results in a product having SAP-particles in undesired locations of the core. Not only SAP-particles are lost during the transfer of the completed core to the conveyor, but also pulp fibers may escape during said transport of the core.

Another way to try to solve the indicated disadvantage would be to increase the vacuum inside the second suction box 5. This could cause the SAP-particles to penetrate deeper into the underlying first layer of pulp fibers and even to be sucked out of the core and clog the air pervious means or to escape into the second suction box 5 and cause problems in the vacuum generation equipment.

OBJECTS AND SUMMARY

The present invention discloses a way to improve the manufacturing process and to provide measures to overcome the indicated disadvantages.

According to a first embodiment of the present invention there is provided an apparatus for manufacturing an absorbent core for an absorbent product containing a first material and a second material dispersed throughout at least a portion of said first material, wherein the apparatus comprises:
- a rotating forming wheel provided with air pervious means along its circumferential surface,
- at least one forming chamber along a first arc of said surface for receiving fibers of said first material and means for directing said fibers of said first material in a stream towards said surface of the forming wheel for depositing a layer of said fibers on said surface,
- at least one of said forming chambers having an inlet for introduction of particles of said second material into said stream for depositing a layer of a mixture of said fibers and said particles on the surface of said wheel, and that
- an air pervious belt is provided along a second arc of the circumferential surface of the forming wheel, wherein said belt bears on the formed at least one layer of said first and second materials and runs at the same speed as the surface of the forming wheel for keeping the fibers and particles of said formed layer or layers in place on the wheel.

According to a second embodiment of the invention there is provided a method for
- manufacturing an absorbent product containing a first material and a second material dispersed throughout at least a portion of said first material, wherein the method comprises the steps of:
- providing a forming wheel having air pervious means along its circumferential surface,
- rotating said forming wheel,
- arranging at least one forming chamber along a first arc of said surface,
- receiving in said forming chamber fibers from said first material,
- directing said fibers of said first material in a stream towards said surface of the forming wheel,
- introducing in at least one of said forming chambers particles of said second material into said stream,
- depositing at least a layer of said first and said second materials on said surface,
- providing at least one mold along said circumferential surface,
- covering said mold along a second arc of the forming wheel with a belt running at substantially the same speed as the forming wheel at the surface of said wheel.

In short, the apparatus is provided with a continuous air pervious belt, which runs together with the forming wheel, substantially at the same speed as the forming wheel at the surface of the forming wheel, where the main purpose of the belt is to cover the continuous layer or molds arranged for the formation of an absorbent core on the circumferential surface of said wheel, such that pulp fibers and particles of the second material are unable to fall out of the core.

An advantage with the various aspects of the inventions is that loss of material will be reduced and particularly loss of the second material will be reduced. Another advantage is that an air flow radially inwards through the air pervious means provided to keep the absorbent core and its fibers and particles within the mold may be reduced as the core is covered with the inventive belt. Further, the underpressure in the second suction box along the arc of the forming wheel where there are no forming chambers will be enforced, which in turn further contributes to better keep the fibers and particles of the layers of the core in place during transport of the core on the surface of the forming wheel. Due to the reduced air flow, the power consumption of the fan related to the second suction box will be reduced. This reduction in power consumption is also valid for production of absorbent cores where there is no addition of particles of a second material. Further, as the loss of fibers and particles is reduced in comparison to prior art design devices, stoppages in production for cleaning of the machinery may be reduced.

Still further objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

EMBODIMENTS OF THE INVENTION

A number of embodiments of the invention will be presented in the following with support of the enclosed figures.

Figure 1:
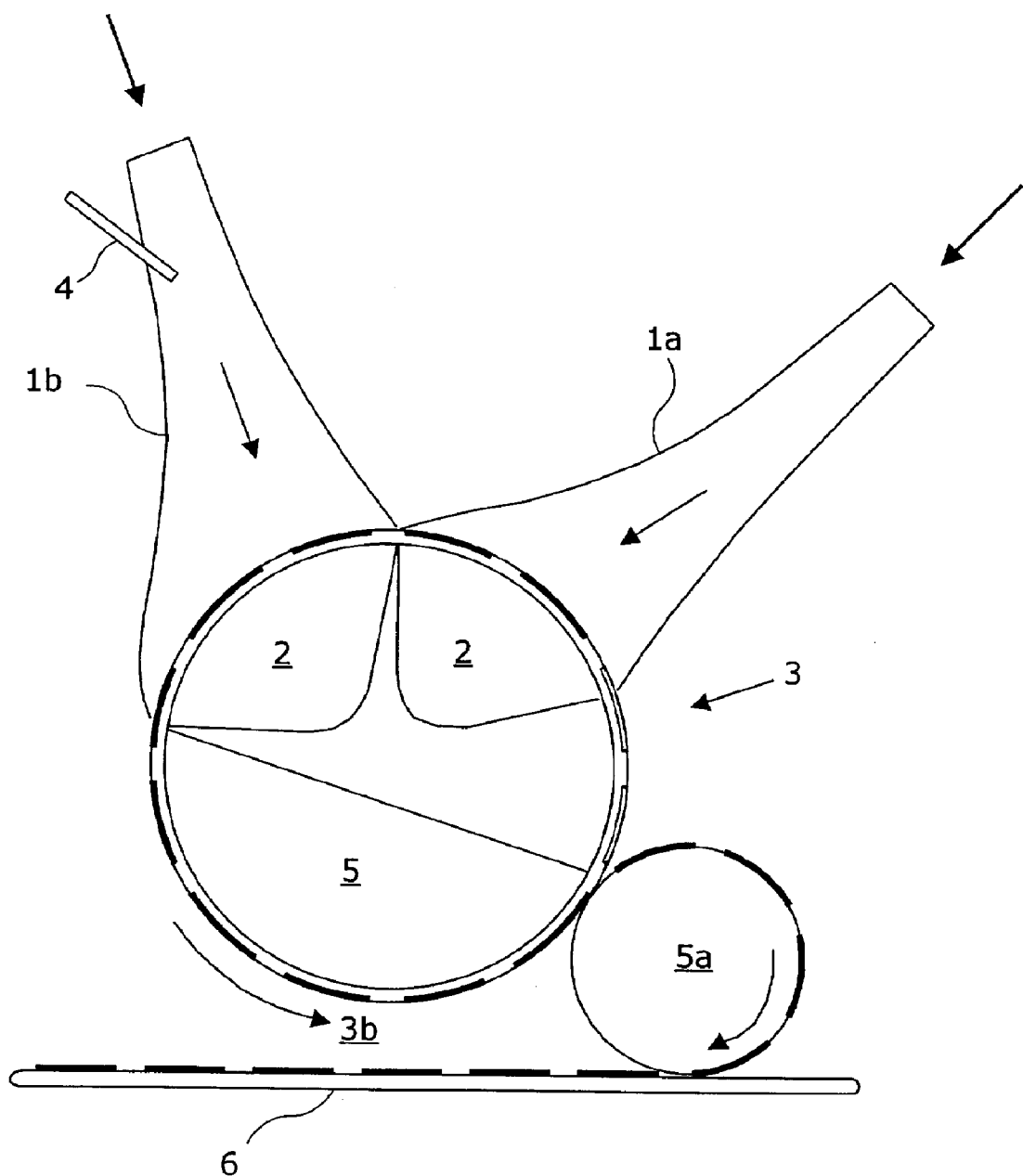
FIG. 1 schematically shows a conventional absorbent core-manufacturing apparatus.
Figure 2:
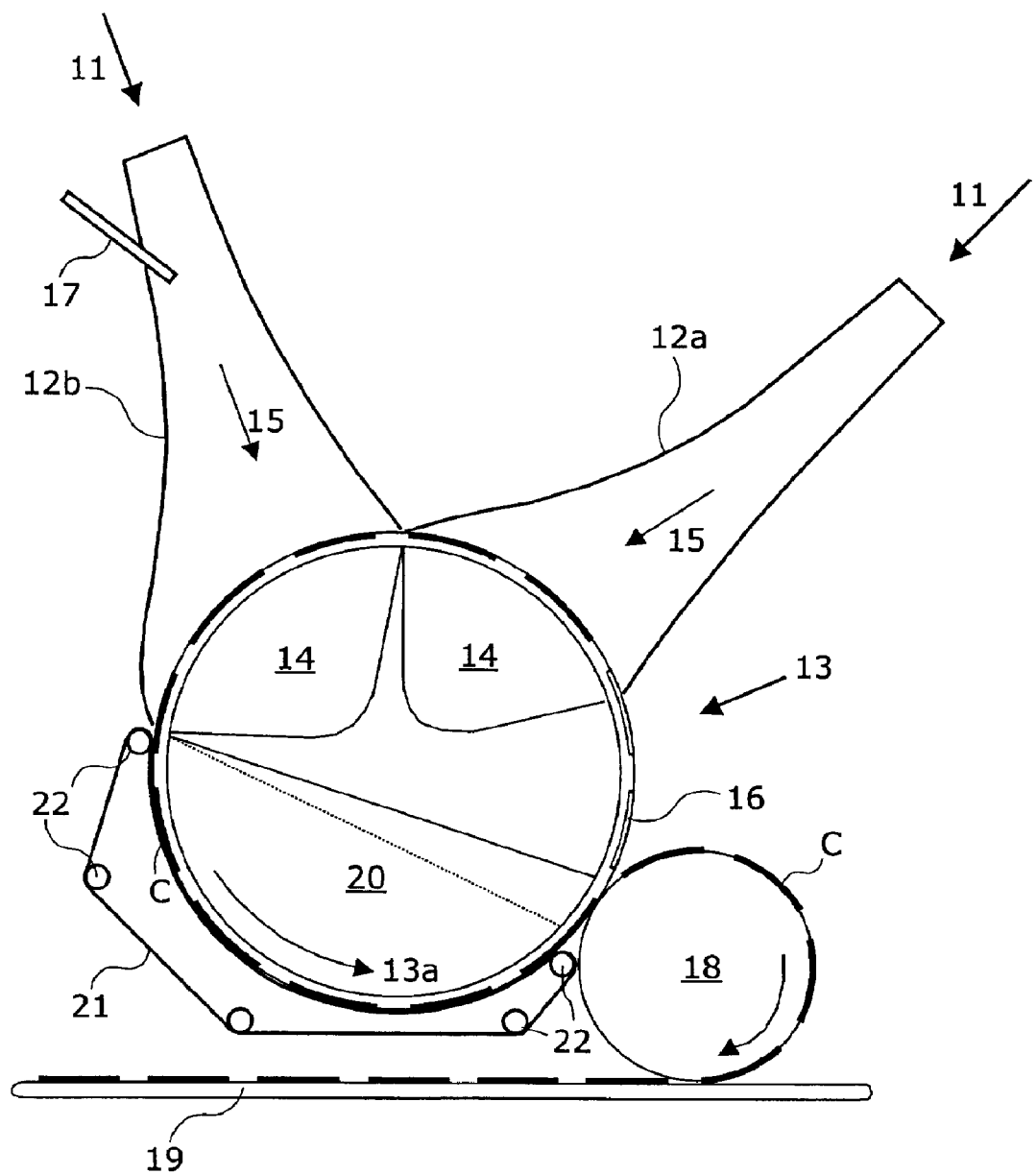
FIG. 2 schematically shows en embodiment of the manufacturing apparatus according to one aspect of the invention.

In FIG. 2, there is disclosed an apparatus for manufacturing an absorbent core of a liquid-absorbent product according to various aspects of the invention. From a defibration unit (not shown) pulp fibers 11 are delivered by the aid of an air stream into forming chambers 12a, 12b, here called hoods. A forming wheel 13 for formation of a core of an absorbent product is arranged to rotate under a downstream opening of a hood 12a, 12b and is in sealed connection with said hood. The forming wheel 13 rotates in the direction shown by arrow 13a. In the embodiment according to the figure, the device is provided with two hoods 12a and 12b. Facing each hood opening, non-rotating first suction boxes 14 are arranged inside the forming wheel 13. An air pervious means is arranged along the circumference of the forming wheel 13 to allow air from said suction boxes 14 to pass radially inwards of the forming wheel. An underpressure prevails in the first suction boxes 14 for sucking air from said hoods 12 through the air pervious means to generate a stream 15 of said radially inwards passing air. Said underpressure may be generated by means of not shown fans.

Fibers delivered to the hoods 12a, 12b are forwarded by the stream 15 towards the circumference of the forming wheel 13 and are deposited there against the air pervious means, which may consist of any net, a plate provided by holes, a fabric or the like.

The forming wheel 13 may be provided with a continuous mold extending along the circumference of the forming wheel. In the figure there is shown an example where a series of separate molds 16 are arranged along the circumference of the forming wheel 13. A continuous mold is utilized when the fibers deposited on the air pervious means are to be used to form a continuous layer, which is subsequently cut into suitable dimensions and shapes to form individual absorbent cores of an absorbent product. Separate molds are used to directly form cores of a special shape and dimension to form an absorbent core of an absorbent product. Variants of molds are known in the art and need not further be discussed herein.

Often the pulp fibers are combined with other fibers or particles with special properties as added ingredients to form the absorbent cores of absorbent products. FIG. 2 gives an example of a way to add such particles, which for example may be superabsorbent particles or heat activatable bonding particles or odour absorbent particles. Super absorbent particles are described, inter alia, in U.S. Pat. No. 4,540,454. In the hood 12a pulp fibers 11, only, are used for forming a first layer of the produced core C in the molds 16. A second hood 12b is provided with an inlet 17, through which the particles to be added are injected to be mixed with the pulp fibers 11 and for being added to the stream 15 to be directed as a mixture of pulp fibers 11 and added particles towards the molds 16 on the forming wheel 13. Hence, as the first formed layer rotates from the first hood 12a and enters the second hood 12b, the mixture of pulp fibers and the added particles forms a second layer on top of the first layer to build up the core of the absorbent product. Instead of injecting the added particles into a hood 12b by means of inlet 17, said hood 12b may be provided with an upstream prepared mixture of pulp fibers 11 and said particles.

According to the prior art technique, as discussed, the completed core in the molds 16 will be transported on the surface of the wheel 13 to a transfer drum 18 and finally to a conveyor belt 19. The transfer drum 18 may be excluded. To keep the core of fibers adhered to the surface of the forming wheel 13, said wheel is provided with a non rotating second suction box 20 inside the wheel 13 and exerting a suction effect on the core, such that it will affix to the surface of the wheel. Said second suction box 20 acts along the surface of the forming wheel from the last one of the forming chambers, the hoods 12a, 12b and as far as the core is transported on the wheel 13. In an alternative embodiment the suction box 20 is not acting along the full second arc of the forming wheel covered by said belt, so that it will be easier to let the core leave the forming wheel (13), when said core is delivered to a transfer drum or a conveyor belt (19), without being sucked to the surface. This alternative embodiment is illustrated by means of the extension of the second suction box being illustrated as a dotted line in FIG. 2.

To prevent fibers, particularly the added particles, from falling out of, or escaping from the formed core of layers, the manufacturing apparatus is provided with a belt 21 arranged in such a way that the belt 21 exerts a pressure against the forming wheel 13 and in particular against the core with the layers of pulp fibers and added particles. By means of this belt 21, the continuous mold or separate molds 16 are covered by said belt and pulp fibers or added particles are prevented from falling out of the mold during delivery of the completed core to the conveyor belt 19 or transfer drum 18.

As is shown in the example according to the figure, the belt 21 is arranged in a closed, endless loop. The belt 21 is mounted on supporting rolls 22 to allow said loop movement. At least one of said supporting rolls 22 is resiliently mounted, making it possible to stretch the belt, so that it will exert a predetermined pressure force against the forming wheel 13.

The belt 21 is preferably air pervious, so that the air sucked radially inwards to the wheel 13 can easily penetrate the belt. The belt is further laterally wide enough to cover the molds 16 in the lateral direction of the forming wheel 13.

The speed of the belt is preferably adapted to be the same as the speed of the circumference of the forming wheel 13, which is self-accomplished as the belt may be driven by the friction forces generated between the belt 21 and the surface of the forming wheel 13, provided that the belt 21 is moving without too much friction in its loop arrangement. If there is too much friction of the belt movement in the belt loop arrangement, the belt and the forming wheel may slide in relation to each other. The belt movement may of course be arranged in such a way that the belt is driven by the forming wheel or by a driving motor, wherein in both cases this could involve a driving of the belt 21 via a gear arrangement.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps, which perform substantially the same function in substantially the same way to achieve the same results, be within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. An apparatus for manufacturing an absorbent product containing a first material and a second material dispersed throughout at least a portion of said first material, the apparatus comprising:

a rotating forming wheel provided with an air pervious means along its circumferential surface, a passage for directing at least a mixture of fibers of said first material and particles of said second material towards the surface of said forming wheel for depositing at least a layer of a mixture of said fibers and said particles along a first arc of the surface of said forming wheel, and an air pervious belt is provided along a second arc of the circumferential surface of the forming wheel, wherein said belt bears on the formed at least one layer of said first and second materials and runs at substantially the same speed as the surface of the forming wheel for keeping the fibers and particles of said formed layer or layers in place on the forming wheel.

2. The apparatus according to claim 1, wherein said passage comprises at least one forming chamber along said first arc of said surface for receiving at least the fibers of said first material and a suction device for directing the fibers of said first material in a stream towards said surface of the forming wheel for depositing a layer of said fibers on said surface and the at least one forming chamber being provided with a mixture of the fibers of said first material and the particles of said second material.

3. The apparatus according to claim 2, wherein the at least one forming chamber being provided with both the fibers of said first material and the particles of the second material has a separate inlet for the introduction of the particles of said second material into said stream.

4. The apparatus according to claim 2, wherein said suction device for directing the fibers towards the forming wheel comprises at least one non-rotating first suction box inside the circumference of the forming wheel, said at least one suction box facing said forming chamber and being provided with an underpressure for generating said stream for sucking the fibers from the forming chamber in the direction of the air pervious surface on the forming wheel.

5. The apparatus according to claim 4, wherein the passage includes a plurality of forming chambers and a first suction box is provided for each of the forming chambers.

6. The apparatus according to claim 1, wherein the first material is pulp fibers.

7. The apparatus according to claim 1, wherein the particles of the second material are particles or fibers of superabsorbent polymer or heat activatable bonding material.

8. The apparatus according to claim 1, wherein said air pervious belt includes at least one member from the group of: a net, a plate provided with holes, an air pervious fabric.

9. The apparatus according to claim 1, wherein the circumferential surface of the forming wheel is provided with a continuous mold or a number of separate molds along the surface.

10. The apparatus according to claim 1, wherein a non-rotating second suction box is provided inside the circumference of the forming wheel, said second suction box being arranged along said second arc of the circumference of the forming wheel and being provided with an underpressure for sucking the formed layer or layers against the air pervious surface of the forming wheel.

11. The apparatus according to claim 10, wherein said belt is arranged to face said second suction box.

12. The apparatus according to claim 11, wherein said suction box extends only a portion of the second arc of the forming wheel covered with the belt.

13. The apparatus according to claim 1, wherein said belt is an endless belt running in a closed loop and supported by supporting rolls.

14. The apparatus according to claim 13, wherein at least one of said supporting rolls is arranged to exert a resilient force on said belt to stretch the belt so that the belt will press against the forming wheel with a predetermined force.

15. The apparatus according to claim 10, wherein the belt has a width broad enough to cover the molds of the forming wheel in a lateral direction.

16. A method for manufacturing an absorbent structure containing a first material and a second material dispersed throughout at least a portion of said first material, the method comprising:
    providing a forming wheel having an air pervious circumferential surface,
    rotating said forming wheel,
    arranging at least one forming chamber along a first arc of said surface,
    receiving in said forming chamber fibers of said first material,
    directing said fibers of said first material in a stream towards said surface of the forming wheel,
    introducing in the at least one forming chamber particles of said second material into said stream,
    depositing at least a layer of said first and said second materials on said surface,
    providing at least one mold along said circumferential surface,
    covering said mold along a second arc of the forming wheel with a belt running at substantially the same speed as the forming wheel at the surface of said wheel.

17. The method according to claim 16, further comprising the step of arranging said belt to be air pervious.

18. The method according to claim 16, further comprising the step of arranging said belt to run in a closed loop.

19. The method according to claim 17, further comprising the step of stretching said belt such that it exerts a pressure against the layer or layers of the first and second material in said at least one mold on said surface.

* * * * *